US008192768B2

(12) United States Patent
Gokaraju et al.

(10) Patent No.: US 8,192,768 B2
(45) Date of Patent: Jun. 5, 2012

(54) SYNERGISTIC ANTI-INFLAMMATORY AND ANTIOXIDANT DIETARY SUPPLEMENT COMPOSITIONS (75) Inventors: Ganga Raju Gokaraju, Vijayawada (IN); Rama Raju Gokaraju, Vijayawada (IN); Trimurtulu Golakoti, Vijayawada (IN); Vendateswarlu Somepalli, Vijayawada (IN)

(73) Assignee: Laila Impex, Vijayawada, IN (US)

( * ) Notice: Subject to any disclaimer, the term of this patent is extended or adjusted under 35 U.S.C. 154(b) by 217 days.

(21) Appl. No.: 12/593,581

(22) PCT Filed: Apr. 3, 2007

(86) PCT No.: PCT/IN2007/000135
§ 371 (c)(1),
(2), (4) Date: Sep. 28, 2009

(87) PCT Pub. No.: WO2008/120220
PCT Pub. Date: Oct. 9, 2008

(65) Prior Publication Data
US 2010/0098676 A1 Apr. 22, 2010

(51) Int. Cl.
A61K 36/00 (2006.01)
A61K 36/82 (2006.01)
(52) U.S. Cl. .................................. 424/725; 424/729
(58) Field of Classification Search .................. None
See application file for complete search history.

(56) References Cited

U.S. PATENT DOCUMENTS

| | | | |
|---|---|---|---|
| 5,494,668 A | 2/1996 | Patwardhan | |
| 5,629,351 A | 5/1997 | Taneja et al. | |
| 6,264,995 B1 | 7/2001 | Newmark et al. | |
| 6,440,468 B1 | 8/2002 | Almagro et al. | |
| 6,521,271 B1 | 2/2003 | Phan | |
| 6,589,516 B1 | 7/2003 | Eyre et al. | |
| 6,841,177 B1 | 1/2005 | Almagro et al. | |
| 6,979,470 B2 | 12/2005 | Babish et al. | |
| 7,884,090 B2* | 2/2011 | Bonner et al. | 514/152 |
| 2003/0096027 A1 | 5/2003 | Babish et al. | |
| 2003/0108628 A1 | 6/2003 | Babish et al. | |
| 2003/0152585 A1 | 8/2003 | Solanki | |
| 2003/0216600 A1 | 11/2003 | Gokaraju et al. | |
| 2004/0166178 A1 | 8/2004 | Meybeck et al. | |
| 2004/0198695 A1* | 10/2004 | Li et al. | 514/54 |
| 2004/0247700 A1 | 12/2004 | Babish et al. | |
| 2005/0123632 A1 | 6/2005 | Chen et al. | |
| 2005/0129791 A1 | 6/2005 | Babish et al. | |
| 2005/0191375 A1 | 9/2005 | Babish et al. | |
| 2005/0282772 A1* | 12/2005 | Gokaraju et al. | 514/54 |
| 2006/0029685 A1* | 2/2006 | Henderson et al. | 424/729 |
| 2006/0040000 A1* | 2/2006 | Gokaraju et al. | 424/725 |
| 2006/0198906 A1 | 9/2006 | Majeed et al. | |

FOREIGN PATENT DOCUMENTS

| | | |
|---|---|---|
| AU | 0075253 | 4/2001 |
| EP | 1133992 | 9/2001 |
| FR | 2655054 A1 | 5/1991 |
| GB | 2388539 A1 | 11/2003 |
| IN | 0182615 | 5/1999 |
| WO | 0057893 A1 | 10/2000 |
| WO | 0059523 A1 | 10/2000 |
| WO | 0062751 A2 | 10/2000 |
| WO | 0195727 A1 | 12/2001 |
| WO | 02083614 A1 | 10/2002 |
| WO | 03007975 A1 | 1/2003 |
| WO | 03077860 A2 | 9/2003 |
| WO | 2005084230 A2 | 9/2005 |
| WO | 2006062681 A1 | 6/2006 |
| WO | 2006095355 A1 | 9/2006 |
| WO | 2007011674 A2 | 1/2007 |

OTHER PUBLICATIONS

Ammon H.P.T et al., Mechanism of antiinflammatory actions of curcumine and bowellic acids, Journal of Ethnopharmacology, 38 (1993) 113-119.
Saura et al., Effect of ascorbic acid and curcumin on quercetin-induced nuclear DNA damage, lipid peroxidation and protein degradation, Cancer Letters, 63 (1992) 237-241.
Ammon H.P.T. et al., Inhibition of Leukotriene 64 Formation in Rat Peritoneal Neutrophils by an Ethanolic Extract of the Gum Resin Exudate of *Boswellia serrata*, Planta Medica 57 (1991) 203-207.
Jiang et al., Use of liquid chromatography—electrospray ionization tandem mass spectrometry to identify diarylheptanoids in turmeric (*Curcuma longa* L.) rhizome, Journal of Chromatography A, 1111 (2006) 21-31.
Nakayama et al., Two Curcuminoid Pigments from *Curcuma domestica*, Phytochemistry, vol. 33, No. 2. pp. 501-502, 1993.
Atal et al., Salaiguggalex-*Boswellia serrata* a promising antihyperlipidemic and antiarthritic agent, Ind. J. Pharm., 1980, 12, 59 (Abstract).
Pachnanda et al., Clinical evaluation of Salai guggal in patients of arthritis, Ind. J. Pharm. 1981, 13, 63 (Abstract).
Singh et al., Pharmacology of an extract of salai guggal ex-*Boswellia serrata*, a new non-steroidal anti-inflammatory agent, Agents Actions, Jun. 18, 1986(3-4): 407-12 (Abstract).
Quiles et. al., *Curcuma longa* Extract Supplementation Reduces Oxidative Stress and Attenuates Aortic Fatty Streak Development in Rabbits, Arteriosclerosis Thromb Vasc Biol 2002, 22:1225-1231 (available at http://atvb.ahajournals.org/content/22/7/1225. viewed on Nov. 9, 2011).

* cited by examiner

Primary Examiner — Christopher R Tate
Assistant Examiner — Randall Winston
(74) Attorney, Agent, or Firm — Kramer & Amado, P.C.

(57) ABSTRACT

Disclosed herein are novel dietary supplement compositions comprising enriched 3-O-acetyl-11-keto-β-boswellic acid and enriched demethylated curcuminoids, wherein the composition exhibits anti-inflammatory, antiulcerogenic and antioxidant activities. Also disclosed are novel compositions comprising enriched 3-O-acetyl-11-keto-β-boswellic acid, enriched demethylated curcuminoids that have a synergistic effect on specific inhibition of—COX-2 and 5-LOX activity and optionally containing glucosamine, resveratrol, garlic extract, chondroitin, methlysulphonymethane, bromelain, serratiopeptidase, quercitine, gallic acid, caffeic acid, green tea extract, aspirin and ibuprofen.

30 Claims, 3 Drawing Sheets

SYNERGISTIC ANTI-INFLAMMATORY AND ANTIOXIDANT DIETARY SUPPLEMENT COMPOSITIONS

FIELD OF THE INVENTION

The present invention relates to synergistic compositions for curing or preventing lipoxygenase mediated and free radical mediated disorders in mammals and various forms of degenerative musculoskeletal diseases such as rheumatoid arthritis and osteoarthritis. The present invention further relates to compositions exhibiting synergistic inhibition of the expression and/or activity of inducible cyclooxygenase-2 (COX-2) and 5-lipoxygenase (5-LOX). Particularly, the compositions comprise of an enriched 3-O-acetyl-11-keto-β-boswellic acid (AKBA), enriched demethylated curcuminoids and optionally containing other ingredients, which shows a synergistic anti-inflammatory and antioxidant property.

BACKGROUND OF THE INVENTION

Inflammatory diseases affect more than fifty million Americans. As a result of basic research in molecular and cellular immunology over the last ten to fifteen years, approaches to diagnosing, treating and preventing these immunologically-based diseases has been dramatically altered. One example of this is the discovery of an inducible form of the cyclooxygenase enzyme. Constitutive cyclooxygenase (COX), first purified in 1976 and cloned in 1988, functions in the synthesis of prostaglandins (PGs) from arachidonic acid (AA). Three years after its purification, an inducible enzyme with COX activity was identified and given the name COX-2, while constitutive COX was termed COX-1.

COX-2 gene expression is under the control of pro-inflammatory cytokines and growth factors. Thus, the inference is that COX-2 functions in both inflammation and control of cell growth. While COX-2 is inducible in many tissues, it is present constitutively in the brain and spinal cord, where it may function in nerve transmission for pain and fever. The two isoforms of COX are nearly identical in structure but have important differences in substrate and inhibitor selectivity and in their intracellular locations. Protective PGs, which preserve the integrity of the stomach lining and maintain normal renal function in a compromised kidney, are synthesized by COX-1. On the other hand, PGs synthesized by COX-2 in immune cells are central to the inflammatory process. The discovery of COX-2 has made possible the design of new drugs and synergistic compositions that reduce inflammation without removing the protective PGs in the stomach and kidney made by COX-1.

Leukotriens and 5(s)-HETE are important mediators for inflammatory, allergic and obstructive process. Leukotriens increases micro vascular permeability and are potent chemo tactic agent. Inhibition of 5-lipoxygenase indirectly reduces the expression of TNF-α. 5-Lipoxygenase is therefore the target enzyme for identifying inhibitors, which have potential to cope with a variety of inflammation and hypersensitivity-based human diseases including asthma, arthritis, bowel diseases such as ulcerative colitis and circulatory disorders such as shock and ischemia.

Free radicals play a major role in the initiation and progression of a wide range of pathological diseases like cancer, Alzheimer's, Parkinson's and cardiovascular disease. In the food industry, free radicals have been found to be responsible in the deterioration of foods during processing and storage. In view of this, considerable attention has been given to the addition of antioxidants in foods and supplementation of antioxidants to biological systems to scavenge free radicals.

A yellow pigmented fraction isolated from the rhizomes of *Curcuma longa* contains curcuminoids belonging to the dicinnamoyl methane group. Curcuminoids are present to the extent of 3 to 5 percent in the raw material. They are considered the most important active ingredients and are believed to be responsible for the biological activity of *Curcuma longa*. Though their major activity is anti-inflammatory, curcuminoids have been reported to possess antioxidant, antiallergic, wound healing, antispasmodic, antibacterial, antifungal, antitumor and antiHIV activity as well. Curcumin was isolated in 1815 and structurally defined in 1910. Other major curcuminoids isolated from *Curcuma longa* include demethoxycurcumin and bisdemethoxycurcumin. Curcuminoids may be found in other botanicals in addition to *Curcuma longa*, such as *Curcuma xanthorrhiza* and *Curcuma zedoaria*. Curcuminoids are well known for their anti-inflammatory activity. Turmeric is one of the oldest anti-inflammatory drugs used in Ayurvedic medicine.

The pharmacokinetics involving the safety, toxicity, dose range and biological properties of turmeric and its components, including curcumin is known, and the turmeric is readily available in various food stores.

The anti-inflammatory properties of curcumin were shown to inhibit the 5-lipoxygenase activity in rat peritoneal neutrophils as well as the 12-lipoxygenase and the cyclooxygenase activities in human platelets (Ammon, H. P. T. et al., *J. Ethopharmacol.*, 1993, 38, 113-119). Curcumin had no significant effect on quercetin-induced nuclear DNA damage, lipid peroxidation and protein degradation and thus has the unique potential of acting as both pro- and antioxidants, depending on the redox state of their biological environment (Saura, C. et al., *Cancer Letters*, 1992, 63, 237-241).

Among the bibliographic references of the most interesting patents existing in the data banks, application FR2,655,054 about the cellular protection agents contained in curcuminoids obtained from *Curcuma longa*, ascorbic acid and/or dismutase super oxide (DSO) stands out. Curcuminoids have a known antioxidizing effect, as well as ascorbic acid and DSO that carry out a synergic effect.

The gum resin of the plant *Boswellia serrata* (Burseraceae) has long been in use for the treatment of rheumatoid arthritis and gout by the practitioners of Ayurvedic medicines in the Indian system of medicine. Various extracts of the gum resin have shown potent anti-inflammatory and anti-arthritic activity in laboratory animals, as well as during clinical trials (Atal, C. K. et al., *Ind. J. Pharm.*, 1980, 12, 59; Pachnanda, V. K. et al., *Ind. J. Pharm.*, 1981, 13, 63). In a detailed pharmacological study, Singh et al have established that the alcoholic extract of *B. serrata* gum resin displayed marked anti-inflammatory activity in carrageenan induced edema in rats and mice and dextran oedema in rats (Singh, G. B. et al., *Agents and Action*, 1986, 18, 407). It has also been recognized in the past that the ethanolic extract of the gum resin of B. serrata inhibits the formation of Leukotriene B4 in rat peritoneal neurophils. Leukotriene B4 is one of the important mediators of inflammatory reactions (Ammon, H. P. T. et al., *Planta Medica*, 1991, 57, 203).

A composition of enriched demethylated curcuminoids, enriched 3-O-acetyl-11-keto-β-boswellic acid (AKBA) and optionally other ingredients for preserving the health of joint tissues, for treating arthritis or other inflammatory conditions with COX-2 and 5-LOX specificity has not yet been discovered. A composition comprising demethylated curcuminoids, AKBA and optionally other ingredients to synergistically inhibit COX-2 and 5-LOX with high specificity and support the normalization of joint function has also not yet been discovered.

An important need therefore exists for dietary composition suitable for human patients that are synergistic in that they have stronger effects than the sum of the effects of the individual components and also synergistic with standard clinical treatment of inflammatory conditions and in the prior art, there is no such synergistic 5-lipoxygenase inhibitory composition for inflammatory diseases.

It is therefore an objective of the present invention to provide a non-toxic dietary supplement composition, which prevents or cure 5-lipoxygenase mediated disorders like inflammatory diseases (e.g. rheumatoid arthritis, osteoarthritis, and periodontal disease), asthama, and bowel disease such as ulcerative colitis and circulatory disorders such as shock and ischemia It is a further objective of the present invention to provide a composition for preventing free radical mediated disorders such as cancer, Alzheimer's, Parkinson's and cardiovascular disease.

Thus, it would be useful to identify an enriched natural composition that would specifically inhibit or prevent the synthesis of COX-2 and 5-LOX. Such a composition, containing enriched demethylated curcuminoids, enriched AKBA, which would be useful for preserving the health of joint tissues, for treating arthritis or other inflammatory conditions, asthma, bowel disease such as ulcerative colitis and circulatory disorders such as shock and ischemia has not previously been discovered.

U.S. Pat. No. 6,521,271 described the methods of promoting improvement of skin condition by administering a turmeric component and glycolic acid to a patient afflicted with a skin disorder.

U.S. Pat. No. 6,264,995 described an herbal composition for reducing inflammation in bones and joints by inhibiting the enzyme cyclooxygenase-2. This composition is prepared from holy basil; turmeric, ginger, green tea, rosemary, huzhang, Chinese goldthread, barberry, oregano and scutellariae baicalensis.

U.S. Pat. No. 6,841,177 disclosed antiproliferative and photosensitization activities of *Curcuma longa* extract and its use in proliferative diseases such as psoriasis, as reducers of plasmatic fibrinogen and the Apolipoprotein B/Apolipoprotein A-1 quotient, without altering other coagulation parameters.

U.S. Pat. No. 6,440,468 disclosed a method for obtaining apolar and polar extracts of *Curcuma* and applications thereof. A process for obtaining the apolar extract comprises: (a) extracting the rhizomes with an organic solvent; (b) filtration and evaporation to dryness of the extract; (c) dissolution of the oleoresin obtained in hot conditions, precipitation while allowing to cool down and filtration of the solid; (d) drying and recrystallizing the solid in order to obtain a product having a purity in curcuminoids higher than 90%. A process for obtaining the polar extract comprises: (i) extraction of the rhizomes with water at 50-70° C. and (ii) filtration and evaporation of the water. Application of the compositions and preparations as catchers of free radicals and anti-ageing agents, as well as reducing agents to reduce the plasma levels of lipid peroxides in human beings are disclosed.

U.S. Pat. No. 5,494,668 disclosed a method of treating degenerative musculoskeletal diseases such as rheumatoid arthritis and osteoarthritis in an animal, typically a human, comprises administering to the animal, typically in a convenient dosage form, a therapeutically effective amount of the beneficiated extracts of the plants ashwagandha (*Withania somnifera*), sallai guggul (*Boswellia serrata*), turmeric (*Curcuma longa*), and ginger (*Zingiber officinale*) in a predetermined proportion relative to each other with or without other biologically active inorganic ingredients, such as zinc sulphate. The beneficiated plant extracts are made in accordance with a novel process which is also disclosed.

U.S. Pat. No. 5,629,351 disclosed a novel fraction comprising a mixture of boswellic acids, wherein the fraction exhibits anti-inflammatory and antiulcerogenic activities. Also disclosed is a novel boswellic acid compound exhibiting anti-inflammatory, antiarthritic and antiulcerogenic activities. Also disclosed is a process for isolating a boswellic acid fraction and individual boswellic acids therefrom.

US Patent Application 20030152585A1 disclosed herbal composition comprising a mixture of herbs such as *Tinospora cordifolia, Aloe Vera, Curcuma longa, Withania somnifera, Achyranthus asperea, Ocimum sanctum* and *Picorrhiza kurroa* for treatment of hematological malignancies.

U.S. Pat. No. 6,979,470 disclosed curcuminoid compositions comprising an effective amount of a curcuminoid species and an effective amount of a diterpene lactone species, a triterpene species or derivatives thereof that have a synergistic effect on specific inhibition of inducible COX-2 activity and have minimal effect on COX-1 activity.

US Patent Application 20040247700A1 disclosed curcuminoid compositions exhibiting synergistic inhibition of the expression and/or activity of cyclooxygenase-2 and this composition is useful for treating e.g. inflammation or arthritis, comprising curcuminoid and diterpene lactone or triterpene, and specifically inhibits inducible cyclooxygenase-2 (COX-2) activity.

US Patent Application 20030096027A1 and 20050129791A1 disclosed curcuminoid compositions exhibiting synergistic inhibition of the expression and/or activity of cyclooxygenase. It is also disclosed this composition for treating e.g. inflammation or inflammation based diseases, comprising curcuminoid species and alpha-acid (hops plant products) or beta-acid (lupulones).

US Patent Application 20030108628A1 described curcuminoid compositions, which exhibits synergistic inhibition of the expression and/or activity of cyclooxygenase. It also disclosed this composition for treating e.g. inflammation or arthritis, comprising curcuminoid and diterpene lactone or triterpene, and specifically inhibits inducible cyclooxygenase-2 (COX-2) activity.

US Patent Application 20050191375A1 described synergistic anti-inflammatory pharmaceutical compositions and related methods using curcuminoids or methylxanthines. It also disclosed the composition for reducing inflammation or treating e.g. pain, cancer, rheumatoid arthritis, psoriasis, ulcerative colitis and conjunctivitis comprises fraction isolated or derived from hops and methylxanthine.

US Patent Application 20050123632A1 described anti-inflammatory activity of a specific turmeric extract. It also disclosed mixture of turmeric oils for pharmaceutical or nutraceutical composition for treating inflammation e.g. rheumatoid arthritis, comprises hexane soluble fraction.

US Patent Application 20030216600A1 described novel polyhydroxy curcumins having antioxidant activity and these new polyhydroxycurcumins are useful as antioxidants.

European Patent 1133992A1 described novel pharmacological activities of *Curcuma longa* extracts. The use of aqueous alcoholic extract of *Curcuma longa* in composition having e.g. photosensitizing, antiproliferative and fibrinogen level reducing activity, used e.g. for treating psoriasis is also disclosed.

The patent WO03007975A1 described curcuminoid compositions, which exhibits synergistic inhibition of the expression and/or activity of cyclooxygenase-2. It also disclosed the composition useful for treating e.g. inflammation or arthritis, comprising curcuminoid and diterpene lactone or triterpene, and specifically inhibits inducible cyclooxygenase-2 (COX-2) activity.

The patent WO06062681A1 described curcuminoid compositions exhibiting synergistic inhibition of the expression and/or activity of cyclooxygenase-2. The formulation comprises, as a first component an effective amount of a curcuminoid species and an effective amount of a second component selected from the group consisting of an alpha-acid species (hops plant products) or beta-acid species (lupulones) or derivatives thereof.

The patent WO05084230A2 described synergistic anti-inflammatory pharmaceutical compositions and related methods using curcuminoids or methylxanthines. The composition useful for reducing inflammation or treating e.g. pain, cancer, rheumatoid arthritis, psoriasis, ulcerative colitis and conjunctivitis comprises fraction isolated or derived from hops and methylxanthine is disclosed.

The patent GB2388539A1 disclosed two polyherbal formulations for treating cancer, comprises mixture of six or four herbs, or mixture of active ingredients extracted or synthesized from herbs. The first formulation comprises a mixture of *Glycine max, Lycopersicon esculentum, Allium sativum, Curcuma longa, Linum usitatissimum* and *Convolvulus arvensis*. The second formulation comprises a mixture of *Tinospora cordifolia, Withania somnifera, Phyllanthus emblica* and *Asparagus racemosus*.

U.S. Pat. No. 5,629,351 described boswellic acid compositions and preparation thereof. The composition comprises a new fraction containing known boswellic acids and new 2-alpha, 3-alpha-dihydroxy urs-12-en-24-oic acid is useful as synergistic anti-inflammatory, antiarthritic and antiulcerogenic agent.

The patent AU0075253A5 described novel pharmacological activities of *Curcuma longa* extracts. The use of aqueous alcoholic extract of *Curcuma longa* in composition having e.g. photosensitizing, antiproliferative and fibrinogen level reducing activity, used e.g. for treating psoriasis is also disclosed.

US patent application 20040166178A1 described 3-O-acetyl-11-keto-boswellic acid or its extract in a topical composition for treatment and prevention of lines and to relax the skin.

The patent also disclosed the use of composition comprising *Boswellia serrata* extract for topical application to the skin, as an agent to soften lines and/or relax the skin.

The patent WO0057893A1 disclosed the composition comprises an extract of *Boswellia* plant and carrier for use on hair and skin for reducing irritation.

The patent WO0062751A2 disclosed the composition comprises *Boswellia* plant extract, carrier and flavor ingredient for treating irritation or inflammation in mouth.

The patent WO03077860A2 disclosed *boswellia* composition comprises an enriched 3-β-acetyl-11-keto-β-boswellic acid (AKBA) for treating e.g. inflammation. It also disclosed a manufacturing process by peracetylating a *boswellia* serrata pentacyclic terpene acidic fraction extract to provide 3-beta-acetoxy-11-keto-beta-boswellic acid.

The patent IN0182615A described a process for the isolation of a new boswellic acid from the gum resin of the plant *boswellia* serrata. It also disclosed the composition for use on hair and skin for reducing irritation comprises extract of *Boswellia* plant and carrier.

U.S. Pat. No. 6,589,516 described compositions containing *Boswellia* extracts. The Composition for use on hair and skin for reducing irritation comprises extract of *Boswellia* plant and carrier is also disclosed.

Thus none of the prior art mentioned above relates to a composition comprising enriched AKBA extracts and enriched demethylated curcuminoids show synergistic 5-lipoxygenase inhibition.

It is therefore an object of the present invention to provide a non-toxic dietary supplement composition, which prevents or cure COX-2 and 5-lipoxygenase mediated disorders, inflammatory diseases like rheumatoid arthritis, periodontal disease, asthma, bowel disease such as ulcerative colitis and circulatory disorders such as shock and ischemia, free radical mediated disorders such as cancer, Alzheimer's, Parkinson's and cardiovascular disease.

SUMMARY OF THE INVENTION

The present invention provides a novel synergistic dietary supplement composition for preventing lipoxygenase mediated and free radical mediated disorders.

The present invention provides a dietary synergistic mixture of enriched 3-O-acetyl 11-keto-β-boswellic acid (AKBA) from *Boswellia serrata*, and enriched demethylated curcuminoids from *Curcuma longa*.

The present invention further provides a dietary synergistic mixture of enriched AKBA from *Boswellia serrata*, and enriched demethylated curcuminoids from *Curcuma longa* and optionally containing one or more of glucosamine, resveratrol, garlic extract, chondroitin, methlysulphonylmethane, bromelain, Serratiopeptidase and quercitine.

The present invention further provides a composition for preventing or curing inflammatory disease like rheumatoid arthritis, osteoarthritis, periodontal disease, asthma, bowel disease such as ulcerative colitis and circulatory disorder such as shock and ischemia.

The present invention further provides a composition for preventing free radical mediated disorders such as cancer, Alzheimer's, Parkinson's, and cardiovascular diseases.

The present invention provides a dietary synergistic mixture of enriched AKBA extract from *Boswellia serrata* and enriched demethylated curcuminoids from *Curcuma longa* wherein the said extract from *Boswellia serrata* is enriched upto 100% of AKBA.

The present invention provides a dietary synergistic mixture of enriched AKBA from *Boswellia serrata*, and enriched demethylated curcuminoid extract from *Curcuma longa* wherein the said extract from *Curcuma longa* is enriched upto 100% of demethylated curcuminoids.

The present invention provides a dietary synergistic mixture of enriched AKBA from *Boswellia serrata*, and enriched demethylated curcuminoids from *Curcuma longa* wherein the said composition functions synergistically to inhibit the inducibility and/or activity of 5-LOX and COX-2.

In our co-pending application US2004073060 dated on 15 Apr. 2004 we have disclosed a process for enriching AKBA in the range of 30-95% from *Boswellia serrata* extract. The enriched AKBA extract is several times more potent 5-Lipoxygenase inhibitor compared to the commercially available *Boswellia* extracts. A detailed study on the structural requirements for boswellic acids indicated that, of all the six acids, 3-O-acetyl-11-keto-β-boswellic acid, hereinafter referenced as AKBA (FIG. 1) shows most pronounced inhibitory activity against 5-LOX.

Figure 1:
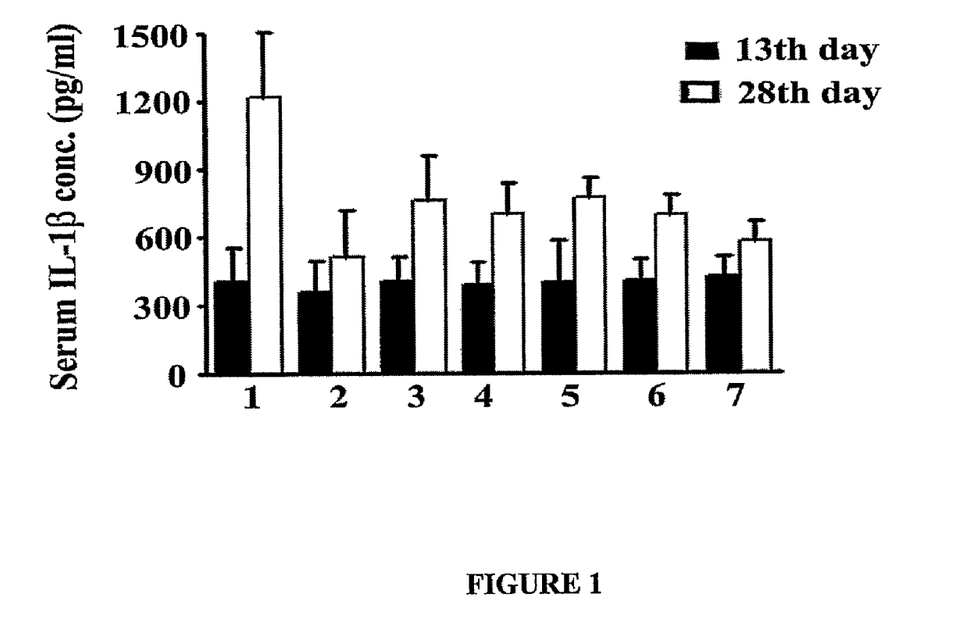

Figure 1. Chemical structure of AKBA

5-Loxin is the brand name for a *Boswellia* extract having not less than 30% of AKBA and this is used to prepare the composition and the extract having 2-95% of AKBA could also be used.

Figure 2:
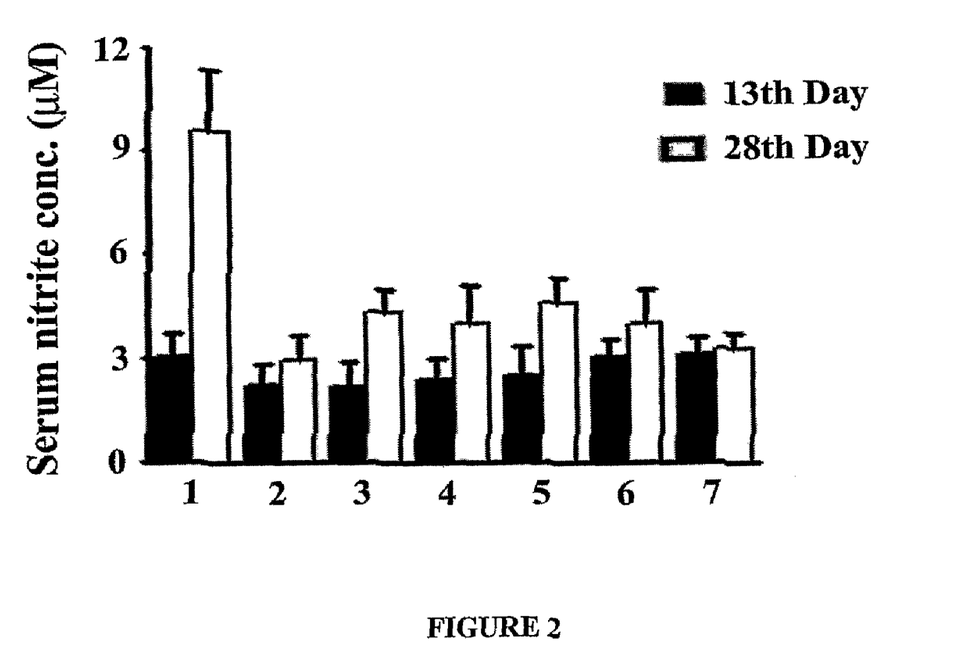

In our co-pending application PCT/IN05/00337 dated on 13 Oct. 2005, we have disclosed a process for enriching demethylated curcuminoids upto 100%. The enriched demethylated curcuminoids is a potent 5-lipoxygenase and free radical inhibitor. The components present in the enriched demethylated curcuminoids are shown in FIG. 2. The demethylated *Curcuma longa* extract having 15-100% of total demethylated curcuminoids (formula 1-4) is used in this composition.

FIG. 2: Chemical structures of the components in enriched demethylated curcuminoids The components present in enriched demethylated curcuminoids are all natural products. The compounds (formula 1, 3 and 4) are present in *Curcuma longa* as minor natural products (Mimura, A. et al., U.S. Pat. No. 5,266,344 and Jiang, H. et al., *J. Chromatography A*, 2006, 1111, 21-31). The compound (formula 2) is isolated from *Curcuma domestica* (Nakayama, R. et al., *Phytochemistry*, 1993, 33, 501-502).

Further, the scientists at National Cancer Institute screened curcuminoids and demethylated curcuminoids for anti-HIV activity. They found that the demethylated curcuminoid (formula 1) inhibited HIV-1 integrase with $IC_{50}$ value below 10 µM.

The mixture having 15-100% of total demethylated curcuminoids (formula 1-4) is used in this composition.

DETAILED DESCRIPTION OF THE INVENTION

The present invention provides compositions and methods for reducing inflammation. In particular, the invention provides a composition having synergistic activity comprising enriched 3-O-acetyl 11-keto-β-boswellic acid (AKBA) derived from *Boswellia serrata*, and enriched demethylated curcuminoids derived from *Curcuma longa*. The invention provides AKBA enriched *Boswellia serrata* extracts in combination with enriched demethylated curcuminoids for use in treating inflammation in a patient prophylactically and/or therapeutically.

The invention is also directed to compositions comprising enriched AKBA from *Boswellia serrata* and enriched demethylated curcuminoids from *Curcuma longa* and optionally containing one or more of glucosamine, resveratrol, garlic extract, chondroitin, methlysulphonymethane and bromelain, serratiopeptidase, and quercitine.

Non-steroidal anti-inflammatory drugs (NSAID's) are most commonly used remedies for rheumatic disease. But regular use of NSAID's increases the development of ulcers in the stomach and duodenum. Hence, there has been a tremendous surge in demand for natural NSAID's because of their established safety and efficacy, through decades of usage by various cultures.

The present inventive composition is composed of natural extracts and proven safety from decades of use in traditional system of medicine. Besides, *Boswellia serrata* extract is known to display antiulcerogenic activity.

In a preferred embodiment, the composition of the invention comprises enriched AKBA and enriched demethylated curcuminoids, and optionally containing glucosamine, resveratrol, garlic extract, chondroitin, methlysulphonymethane and bromelain, serratiopeptidase, and quercitine.

In a preferred embodiment of the invention, the composition of the invention comprises 2-95% of 3-O-acetyl-11-keto-β-boswellic acid.

In a more preferred embodiment of the present invention, the enriched *boswellia* extract contains 30% AKBA, commercially known as 5-Loxin®.

The synergistic new dietary supplement composition comprising enriched AKBA and enriched demethylated curcuminoids is in the ratio of 9:1 to 1:9.

In a preferred embodiment of the invention, the composition comprises enriched 3-O-acetyl-11-keto-β-boswellic acid (AKBA) and enriched demethylated curcuminoids in the ration of 5:1 to 1:1 (w/w) shows synergistic 5-lipoxygenase inhibitory activity (Table 1).

The said dietary supplement composition optionally contains one or more of glucosamine, resveratrol, garlic extract, ginger extract, chondroitin, methysulfonylmethane and bromelain, serratiopeptidase, and quercitine.

The said glucosamine is selected from glucosamine hydrochloride or glucosamine sulphate or N-acetylglucosamine.

The composition for dietary oral supplementation use comprising 10-90% of enriched AKBA extract and 90-10% of enriched demethylated curcuminoids.

The composition for dietary oral supplementation use comprising 30-50% of enriched AKBA extract, 10-20% of enriched demethylated curcuminoids and 40-50% glucosamine hydrochloride.

The said dietary supplement composition contains 30-40% of enriched AKBA extract, 5-20% of enriched demethylated curcuminoids, 50-60% of glucosamine hydrochloride and 5-10% of resveratrol.

The composition for dietary oral supplementation use comprising 30-60% of enriched AKBA extract, 5-20% of enriched demethylated curcuminoids and 5-20% of resveratrol.

The composition for dietary oral supplementation use comprising 30-60% of enriched AKBA extract, 5-20% of enriched demethylated curcuminoids and 10-30% of methylsulfonylmethane.

The composition for dietary oral supplementation use comprising 30-60% of enriched AKBA extract, 5-20% of enriched demethylated curcuminoids and 10-30% of ginger extract.

The composition for dietary supplementation use comprising 20-30% of enriched AKBA extract, 5-10% of enriched demethylated curcuminoids, 40-50% of glucosamine hydrochloride, 5-10% of resveratrol, 10-15% of garlic extract and 10-15% of ginger extract.

The composition comprising 20-30% of enriched AKBA extract, 5-10% of enriched demethylated curcuminoids, 30-40% of glucosamine hydrochloride, 5-10% of chondroitin sulfate, 10-15% of methylsulfonylmethane and 5-10% of bromelain is for dietary supplementation use.

The invention also provides compositions having good antioxidant activity for pharmaceutical or dietary/nutraceutical or cosmetic use, characterized by comprising, enriched AKBA, enriched demethylated curcuminoids, gallic acid, caffeic acid and green tea extract.

The said dietary supplement composition contains 30-50% of enriched AKBA extract, 5-10% of enriched demethylated curcuminoids, 5-10% of gallic acid, 5-10% of caffeic acid and 20-30% of green tea extract.

Further, the invention relates to the composition comprising enriched AKBA from *Boswellia serrata*, and enriched demethylated curcuminoids derived from *Curcuma longa*, and optionally containing one or more of non-steroidal anti-inflammatory agents like aspirin (acetyl salicylic acid), ibuprofen [a-methyl-4-(2-methylpropyl)benzeneacetic acid], etc.

The said dietary supplement composition contains 30-50% of enriched AKBA extract, 5-20% of enriched demethylated curcuminoids and 10-30% of aspirin.

The said dietary supplement composition contains 30-50% of enriched AKBA extract, 5-20% of enriched demethylated curcuminoids and 10-30% of ibuprofen.

The said synergistic dietary supplement composition comprising enriched AKBA and enriched demethylated curcuminoids and optionally containing other ingredients is found to show good antioxidant activity (Table 2).

A method of treating a subject suffering from an inflammatory disease, wherein said inflammatory disease result from biomolecules secreted from activated and degranulated mast cells, said inflammatory disease being selected from the group consisting of osteoarthritis, cancer, fibromyalgia, atherosclerosis, inflammatory bowel disease, interstitial cystitis, irritable bowel syndrome, asthama, migraines, angina, chronic prostatitis, eczema, arthritis, multiple sclerosis, psoriasis, sun burn, and periodontal disease, comprising the step of administering to said subject an effective amount (e.g., an amount effective to treat, slow the progression of, etc) of said composition.

A method of preventing a subject suffering from free radical mediated disease, wherein said free radical mediated disease result from the radicals generated in the body, said free radical disease being selected from cancer, Alzheimer's, Parkinson's, and cardiovascular diseases comprising the step of administering to said subject an effective amount of the said composition.

Active new dietary supplement composition of the present invention may be produced by the procedures described herein or variations thereof, which will apparent to those skilled in the art.

A further aspect of the present invention describes a pharmaceutical formulation comprising a composition along with in a pharmaceutically acceptable carrier (eg, an aqueous or a non aqueous carrier).

Preferred embodiments relating to the different compositions of the subject invention are illustrated below:

Composition 1: A dietary supplement composition was prepared by mixing unit doses of the following components:

| | |
|---|---|
| Enriched AKBA extract | 5 g |
| Enriched demethylated curcuminoids | 1 g |

Composition 2: A dietary supplement composition was prepared by mixing unit doses of the following components:

| | |
|---|---|
| Enriched AKBA extract | 5 g |
| Enriched demethylated curcuminoids | 1 g |

Composition 3: A dietary supplement composition was prepared by mixing unit doses of the following components:

| | |
|---|---|
| Enriched AKBA extract | 2 g |
| Enriched demethylated curcuminoids | 2 g |

Composition 4: A dietary supplement composition was prepared by mixing unit doses of the following components:

| | |
|---|---|
| Enriched AKBA extract | 2 g |
| Enriched demethylated curcuminoids | 0.5 g |
| Glucosamine hydrochloride | 2.5 g |

Composition 5: A dietary supplement composition was prepared by mixing unit doses of the following components:

| | |
|---|---|
| Enriched AKBA extract | 1.5 g |
| Enriched demethylated curcuminoids | 0.25 g |
| Glucosamine hydrochloride | 3 g |
| Resveratrol | 0.25 g |

Composition 6: A dietary supplement composition was prepared by mixing unit doses of the following components:

| | |
|---|---|
| Enriched AKBA extract | 1.5 g |
| Enriched demethylated curcuminoids | 0.25 g |
| Glucosamine hydrochloride | 2 g |
| Resveratrol | 0.25 g |
| Garlic extract | 1 g |

Composition 7: A dietary supplement composition was prepared by mixing unit doses of the following components:

| | |
|---|---|
| Enriched AKBA extract | 1.5 g |
| Enriched demethylated curcuminoids | 0.25 g |
| Glucosamine hydrochloride | 2 g |
| Resveratrol | 0.25 g |
| Garlic extract | 0.75 g |
| Ginger extract | 0.75 g |

Composition 8: A dietary supplement composition was prepared by mixing unit doses of the following components:

| | |
|---|---|
| Enriched AKBA extract | 2.5 g |
| Enriched demethylated curcuminoids | 0.5 g |
| Gallic acid | 0.5 g |
| Caffeic acid | 0.5 g |
| Green tea extract | 1 g |

The invention is further explained with the help of the following examples:

EXAMPLE 1

Synergestic 5-lipoxygenase Inhibitory Activity

The new dietary supplement compositions are screened for their 5-lipoxygenase inhibitory potential using colorimetric method. The assay mixture contained 50 mM phosphate buffer (pH 6.3), 5-lipoxygenase, various concentrations of test composition (5 µg, 10 µg, 20 µg) in dimethylsulphoxide and linolenic acid in a total volume of 0.5 mL, after 5 min incubation of above reaction mixture 0.5 mL ferric xylenol orange reagent is added and OD is measured after two minutes at 585 nm using spectrophotometer. Controls are run along with test in a similar manner except using vehicle instead of test substance solution. Percent inhibition is calculated by comparing absorbance of test solution with that of control.

The results are illustrated in the following table

TABLE 1

5-Lipoxygenase inhibitory activity

| | | % of inhibition | | |
|---|---|---|---|---|
| S. No. | Name of the compound | 5 µg | 10 µg | 20 µg |
| 1 | Composition 1 | 22.4 | 34.1 | 49.7 |
| 2 | Composition 2 | 29.3 | 39.9 | 49.2 |
| 3 | Composition 3 | 44.5 | 57.5 | 64.14 |
| 4 | Composition 4 | 19.4 | 27.3 | 45.1 |
| 5 | Composition 5 | 9.1 | 14.9 | 34.9 |
| 6 | Composition 6 | 15.6 | 22.7 | 36.5 |
| 7 | Composition 7 | 17.1 | 24.1 | 44.5 |
| 8 | Composition 8 | 12.5 | 25.6 | 53.2 |
| 9 | Enriched AKBA extract | 0 | 12.5 | 32.7 |
| 10 | Enriched demethylated curcuminoids | 33.9 | 62.9 | 67.5 |

The higher the % inhibition values, the higher the activity.

From the above 5-lipoxygenase inhibitory values (Table 1), it clearly shows the synergism of the compositions. For example, at 5 µg concentration, the enriched demethylated curcuminoids and enriched AKBA extract exhibited 33.9% and 0% inhibition respectively. Whereas the composition 3, which contains 1:1 ratio of enriched demethylated curcuminoids and enriched AKBA extract exhibited 44.5% inhibition. This inhibitory value of the composition is higher than the individual components.

EXAMPLE 2

Antioxidant Activity of the Compositions

The dietary supplement compositions are screened for their antioxidant activity by superoxide free radical-scavenging method. The superoxide free radical-scavenging activity is determined by the NBT (nitro blue tetrazolium) method. The reaction mixture contained EDTA (6.6 mM), NaCN (3 µm), riboflavin (2 NBT (50 µM), various concentrations of the test compositions in ethanol and a phosphate buffer (58 mM, pH 7.8) in a final volume of 3 ml. Optical density is measured at 560 nm. The test tubes are uniformly illuminated with an incandescent lamp for 15 min, after which the optical density is measured again at 560 nm. The percentage inhibition and superoxide radical generation is measured by comparing the absorbance values of the control and those of the test compounds.

The dietary supplement compositions are screened for their antioxidant activity by DPPH method. DPPH (1,1-diphenyl-2-picrylhydrazyl) radical scavenging activity is measured based on the reduction of methanolic solution of the colored DPPH. Free radical scavenging ability of the test compositions in ethanol added to the methanolic solution of DPPH is inversely proportional to the difference in initial and final absorption of DPPH solution at 516 nm. The reaction mixture contained $1\times10^{-4}$ mM methanolic solution of DPPH and various concentrations of test drugs. The percentage inhibition is determined by comparing the absorbance values of test and control tubes.

The results are illustrated in the following table:

TABLE 2

Antioxidant activity

| S. No. | Name of the compound | Superoxide (NBT) $IC_{50}$ µg | DPPH $IC_{50}$ µg |
|---|---|---|---|
| 1 | Composition 1 | 26.0 | 2.88 |
| 2 | Composition 2 | 16.5 | 2.62 |
| 3 | Composition 3 | 7.5 | 1.33 |
| 4 | Composition 4 | 50.0 | 13.06 |
| 5 | Composition 5 | 73.0 | 28.75 |
| 6 | Composition 6 | 79.6 | 26.85 |
| 7 | Composition 7 | 74.0 | 27.43 |
| 8 | Composition 8 | 8.75 | 4.64 |
| 9 | Enriched AKBA extract | >100 | — |
| 10 | Enriched demethylated curcuminoids | 2.8 | — |

The lower the $IC_{50}$ values, the higher the antioxidant activity.

The above antioxidant activity data (Table 2) reveled that all the compositions exhibited good antioxidant activity. Further, these compositions are potent antioxidant agents in comparison with commercially available antioxidants like Vitamin E etc.

EXAMPLE 3

Synergestic anti-inflammatory activity of composition-1: Test animals (rats, 200-300 g) of either sex were randomly distributed into different groups, with 5 animals in each group. Rats were supplemented daily with either demethylated curcuminoids (50 mg/kg) or enriched AKBA extract (50 mg/kg) or composition 1 (50 mg/kg) in 1% CMC for 28 days. The control group received same volume of vehicle (1% CMC), a standard drug, prednisolone (10 mg/kg, orally) was used in the control treatment group. On the day 14, 100 µl of Freund's Complete Adjuvant (FCA) was injected subcutaneously in the sub planter region of the left hind paw. Blood samples were collected from each animal on the previous day of FCA challenge and at the day of termination of experiment i.e. 14 days after challenge. At the 28th day paw volumes were measured and after sacrificing the animals, liver tissues were excised and stored at −80° C. until further use. The pro-inflammatory markers like nitrite, IL-1β in sera, and paw edema were measured.

EXAMPLE 4

Synergestic anti-inflammatory activity of composition 7. Test animals (rats, 200-300 g) of either sex were randomly distributed into different groups, with 5 animals in each group. Rats were supplemented daily with either demethylated curcuminoids (50 mg/kg) or enriched AKBA extract (50 mg/kg) or glucosamine (50 mg/kg), or reseveratrol (50 mg/kg), garlic extract (50 mg/kg) or ginger extract (50 mg/kg), or composition 7 (50 mg/kg) in 1% CMC for 28 days. The control group received same volume of vehicle (1% CMC); a standard drug, Prednisolone (10 mg/kg, orally) was used in the control treatment group. On the day 14, 100 µl of Freund's Complete Adjuvant (FCA) was injected subcutaneously in the sub planter region of the left hind paw. Blood samples were collected from each animal on the previous day of FCA challenge and at the day of termination of experiment i.e. 14 days after challenge. At the 28th day paw volumes were measured and after sacrificing the animals, liver tissues were excised and stored at −80° C. until further use.

The percent of inhibitions are as follows:

| | |
|---|---|
| Demethylated curcuminoids | 42.3% |
| Enriched AKBA extract | 36.5% |
| Glucosamine | 5.5% |
| Reseveratrol | 20.5% |
| Garlic extract | 25.2% |
| Ginger extract | 20.2% |
| Composition 7 | 49.5% |

DESCRIPTION OF DRAWINGS

The results are summarized in FIGS. 1, 2 and 3 for IL-1β, nitrite and edema volume respectively.

FIG. 1 depicts bar diagrammatic representation of modulation of serum IL-1b concentration (pg/ml) in different groups of animals on the 13th day (before FCA challenge) and on the 28th day (14 days after challenge) of experiment. 1, CMC control; 2, Prednisolone; 3, Curcuminoids 95% (50 mg/kg body weight); 4, demethylated curcuminoids (10 mg/kg); 5, enriched AKBA extract (50 mg/kg); 6, a mixture of natural curcuminoids and enriched AKBA extract (50 mg/kg); 7, Composition 1 (50 mg/kg). Each bar represents mean±SD obtained from 5 animals in each group.

FIG. 2 shows bar diagrammatic representation of modulation of serum nitrite concentration (mM) in different groups of animals on the 13th day (before FCA challenge) and on the 28th day (14 days after challenge) of experiment. 1, CMC control; 2, Prednisolone; 3, Curcuminoids 95% (50 mg/kg body weight); 4, demethylated curcuminoids (10 mg/kg); 5, enriched AKBA extract (50 mg/kg); 6, a mixture of natural curcuminoids and enriched AKBA extract (50 mg/kg); 7, composition 1 (50 mg/kg). Each bar represents mean±SD obtained from 5 animals in each group.

Figure 3:
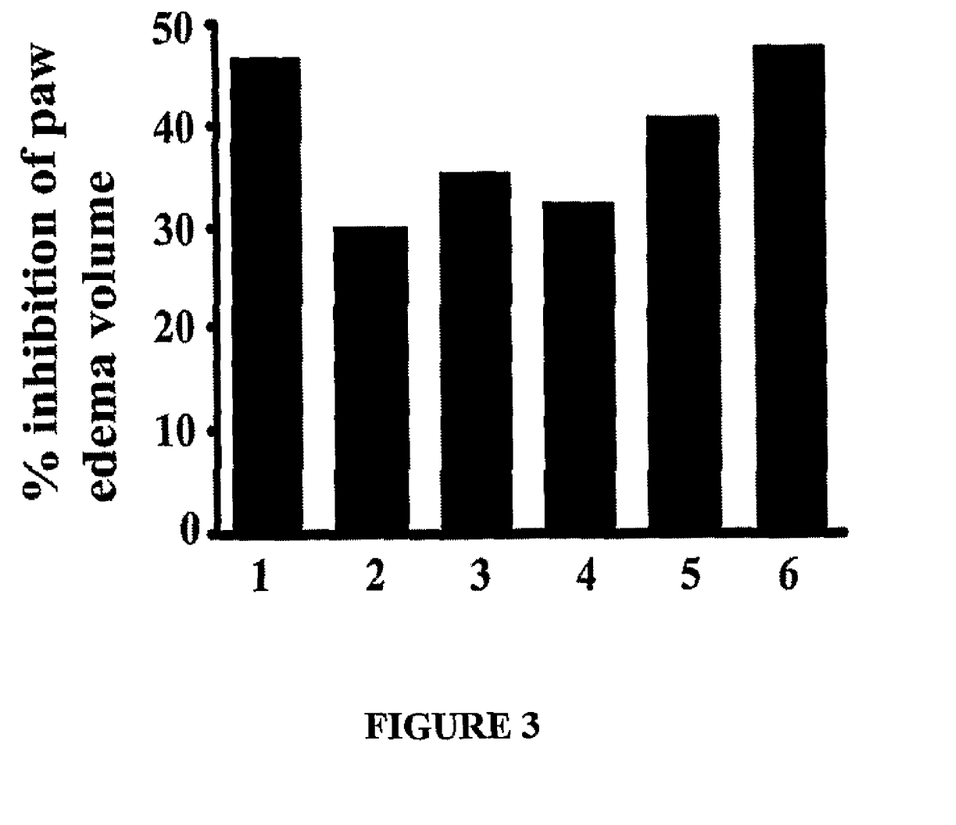

FIG. 3 shows bar diagrammatic representation of percent inhibition of paw edema after 14 days of inoculation of Freund complete adjuvant inoculation in sub planter region of the left hind paw in animals of different groups. 1, Prednisolone; 2, Curcuminoids 95% (50 mg/kg body weight); 3, demethylated curcuminoids (10 mg/kg); 4, enriched AKBA extract (50 mg/kg); 5, a mixture of natural curcuminoids and enriched AKBA extract (50 mg/kg); 6, composition 1 (50 mg/kg). Each bar represents the mean value in percent inhibition with respect to CMC control group.

It will be evident to those skilled in the art that the invention is not limited to the details of the foregoing illustrative example and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

We claim:
1. A composition for treating 5-lipoxygenase mediated diseases and free radical mediated diseases comprising an effective amount of a *Boswellia serrata* extract containing 3-O-acetyl-11-keto-β-boswellic acid (AKBA) and an effective amount of enriched demethylated curcuminoids obtained from a *Curcuma longa* extract, said compositions optionally containing at least one of:
   a) a compound selected from the group consisting of glucosamine, resveratrol, garlic extract, ginger extract, chondroitin, methylsulfonylmethane, bromelain, serratia peptidase, quercitine, and mixtures thereof,
   b) natural antioxidants selected from the group consisting of gallic acid, caffeic acid, green tea extract, and mixtures thereof, and
   c) non-steroidal anti-inflammatory agents selected from the group consisting of aspirin and ibuprofen,
   said demethylated curcuminoids comprising from 15% to 100% by weight of at least one compound selected from the group consisting of compounds of Formula 1, Formula 2, Formula 3 and Formula 4:

-continued

Formula 3

Formula 4

2. The composition as claimed in claim 1, wherein said extract containing AKBA is an enriched *Boswellia serrata* extract containing 2-95% of 3-O-acetyl-11-keto-β-boswellic acid.

3. The composition as claimed in claim 1, wherein the enriched demethylated curcuminoids are obtained by demethylation of *Curcuma longa* extract.

4. The composition as claimed in claim 1, wherein the glucosamine is selected from the group consisting of glucosamine hydrochloride, glucosamine sulphate, and N-acetylglucosamine.

5. The composition as claimed in claim 2, comprising 10-90% of said enriched *Boswellia serrata* extract and 90-10% of enriched demethylated curcuminoids.

6. The composition as claimed in claim 2, comprising 30-50% of said enriched *Boswellia serrata* extract, 10-20% of enriched demethylated curcuminoids and 40-50% of glucosamine hydrochloride.

7. The composition as claimed in claim 2, comprising 30-60% of said enriched *Boswellia serrata* extract, 5-20% of enriched demethylated curcuminoids; and 5-20% of resveratrol.

8. The composition as claimed in claim 2, comprising 30-60% of said enriched *Boswellia serrata* extract, 5-20% of enriched demethylated curcuminoids and 10-30% of methylsulfonylmethane.

9. The composition as claimed in claim 2, comprising 30-60% of said enriched *Boswellia serrata* extract, 5-20% of enriched demethylated curcuminoids and 10-30% of ginger extract.

10. The composition as claimed in claim 2, comprising 20-30% of said enriched *Boswellia serrate* extract, 5-10% of enriched demethylated curcuminoids, 40-50% of glucosamine hydrochloride, 5-10% of resveratrol, 10-15% of garlic extract, and 10-15% of ginger extract.

11. The composition as claimed in claim 2, comprising 20-30% of said enriched *Boswellia serrata* extract, 5-10% of enriched demethylated curcuminoids, 30-40% of glucosamine hydrochloride, 5-10% of chondroitin sulfate, 10-15% of methylsulfonylmethane and 5-10% of bromelain.

12. A composition according to claim 1, wherein the composition comprises one or more natural antioxidants selected from the group consisting of gallic acid, caffeic acid and green tea extract.

13. The composition as claimed in claim 12, comprising 30-50% of said extract containing AKBA, 5-10% of enriched demethylated curcuminoids, 5-10% of gallic acid, 5-10% of caffeic acid and 20-30% of green tea extract.

14. A composition according to claim 1, wherein the composition comprises one or more non-steroidal anti-inflammatory agents selected from the group consisting of aspirin and ibuprofen.

15. The composition as claimed in claim 14, comprising 30-50% of said extract containing AKBA, 5-20% of enriched demethylated curcuminoids and 10-30% of aspirin.

16. The composition as claimed in claim 14, comprising 30-50% of said extract containing AKBA, 5-20% of enriched demethylated curcuminoids and 10-30% of ibuprofen.

17. The composition as claimed in claim 1 in the form of therapeutic formulations for treating inflammatory conditions.

18. The composition as claimed in claim 1 in the form of therapeutic formulation for treating free radical mediated disorders.

19. The composition as claimed in claim 1 in the form of therapeutic formulations for treating cardiovascular diseases.

20. The composition as claimed in claim 1 in the form of dietary or nutraceutical formulations.

21. The composition as claimed in claim 1 in the form of cosmetic formulations.

22. A pharmaceutical formulation comprising a composition according to claim 1 and a pharmaceutical acceptable carrier.

23. The pharmaceutical formulation according to claim 22, wherein said carrier is an aqueous or non-aqueous carrier.

24. The composition as claimed in claim 1, comprising 30-40% of said extract containing AKBA, 5-10% of enriched demethylated curcuminoids and 50-60% of glucosamine hydrochloride and 5-10% of resveratrol.

25. The composition as claimed in claim 1, wherein the extract containing AKBA is an enriched *Boswellia serrata* extract containing 30% of 3-O-acetyl-11-keto-β-boswellic acid.

26. A composition according to claim 1, wherein the composition comprises a compound selected from the group consisting of glucosamine, resveratrol, garlic extract, ginger extract, chondroitin, methylsulfonylmethane, bromelain, serratia peptidase, quercitine, and mixtures thereof.

27. A method of treating a subject suffering from an inflammatory disease, wherein said inflammatory disease result from biomolecules secreted from activated and degranulated mast cells, said inflammatory disease being selected from the group consisting of osteoarthritis, cancer, fibromyalgia, atherosclerosis, inflammatory bowel disease, interstitial cystitis, irritable bowel syndrome, migraines, angina, chronic prostatitis, eczema, arthritis, multiple sclerosis, psoriasis, sun burn, and periodontal disease, comprising the step of administering to said subject an effective amount of a composition according to claim 1.

28. A method of treating a subject suffering from an inflammatory disease mediated by 5-lipoxygenase enzyme comprising the step of administering to said subject an effective amount of a composition according to claim 1.

29. A composition for treating 5-lipoxygenase mediated diseases and free radical mediated diseases, comprising:
   an effective amount of an extract of *Boswellia serrata*, said extract of *Boswellia serrata* being enriched in 3-O-acetyl-11-keto-β-boswellic acid (AKBA);
   an effective amount of an extract of *Curcuma longa*, said extract of *Curcuma longa* being enriched in demethylated curcuminoids;
   an optional compound selected from the group consisting of glucosamine, resveratrol, garlic extract, ginger extract, chondroitin, methylsulfonylmethane, bromelain, serratia peptidase, quercitine, and mixtures thereof;

an optional antioxidant selected from the group consisting of gallic acid, caffeic acid, green tea extract, and mixtures thereof; and an optional non-steroidal anti-inflammatory agents selected from the group consisting of aspirin and ibuprofen;

said demethylated curcuminoids comprising from 15% to 100% by weight of at least one compound selected from the group consisting of compounds of Formula 1, Formula 2, Formula 3 and Formula 4:

Formula 1

Formula 2

Formula 3

Formula 4

30. A composition for treating 5-lipoxygenase mediated diseases and free radical mediated diseases, comprising:

an effective amount of 3-O-acetyl-11-keto-β-boswellic acid (AKBA); and an effective amount of demethylated curcuminoids;

said demethylated curcuminoids comprising from 15% to 100% by weight of at least one compound selected from the group consisting of compounds of Formula 1, Formula 2, Formula 3 and Formula 4:

Formula 1

Formula 2

Formula 3

Formula 4

* * * * *

UNITED STATES PATENT AND TRADEMARK OFFICE
CERTIFICATE OF CORRECTION

PATENT NO. : 8,192,768 B2
APPLICATION NO. : 12/593581
DATED : June 5, 2012
INVENTOR(S) : Ganga Raju Gokaraju et al.

Page 1 of 1

It is certified that error appears in the above-identified patent and that said Letters Patent is hereby corrected as shown below:

On the Title page of the patent, Item (75), line 4, replace "Vendateswarlu" with "Venkateswarlu".

On the Title page of the patent, in the Abstract, Item (57), line 10, replace "methlysulphonymethane" with "methylsulphonylmethane".

In Col. 8, line 46, replace "methlysulphonymethane" with "methylsulphonylmethane".

In Col. 8, line 67, replace "N-acetylyglucosamine" with "N-acetylglucosamine".

In Col. 9, line 48, replace "[a-methyl-4-(2-methylpropyl)benzeneacetic acid]" with "[alpha-methyl-4-(2-methylpropyl)benzeneacetic acid]".

In Col. 12, line 19, replace the text from the word "riboflavin" to the word "various" with the following text: "riboflavin (2 micromolar), NBT (50 micromolar), various".

In Col. 14, claim 1, line 41, replace "quercitine" with "quercetine".

In Col. 15, claim 10, line 2, replace "Boswellia serrate" with "Boswellia serrata".

Signed and Sealed this
Eleventh Day of December, 2012

David J. Kappos
*Director of the United States Patent and Trademark Office*

UNITED STATES PATENT AND TRADEMARK OFFICE
CERTIFICATE OF CORRECTION

PATENT NO. : 8,192,768 B2  
APPLICATION NO. : 12/593581  
DATED : June 5, 2012  
INVENTOR(S) : Ganga Raju Gokaraju et al.

Page 1 of 1

It is certified that error appears in the above-identified patent and that said Letters Patent is hereby corrected as shown below:

On the Title page of the patent, Item (75), line 4, replace "Vendateswarlu" with "Venkateswarlu".

On the Title page of the patent, in the Abstract, Item (57), line 10, replace "methlysulphonymethane" with "methylsulphonylmethane".

In Col. 8, line 46, replace "methlysulphonymethane" with "methylsulphonylmethane".

In Col. 8, line 67, replace "N-acetylyglucosamine" with "N-acetylglucosamine".

In Col. 9, line 48, replace "[a-methyl-4-(2-methylpropyl)benzeneacetic acid]" with "[alpha-methyl-4-(2-methylpropyl)benzeneacetic acid]".

In Col. 12, line 19, replace the text from the word "riboflavin" to the word "various" with the following text: "riboflavin (2 micromolar), NBT (50 micromolar), various".

In Col. 14, line 41 (claim 1, line 11), replace "quercitine" with "quercetine".

In Col. 15, line 50 (claim 10, line 2), replace "Boswellia serrate" with "Boswellia serrata".

This certificate supersedes the Certificate of Correction issued December 11, 2012.

Signed and Sealed this  
First Day of January, 2013

David J. Kappos  
*Director of the United States Patent and Trademark Office*